United States Patent [19]

Palti

[11] 4,269,222
[45] May 26, 1981

[54] CONSTANT FLOW DEVICE

[76] Inventor: Yoram Palti, 51 Ruth St., Haifa, Israel

[21] Appl. No.: 24,389

[22] Filed: Mar. 27, 1979

[51] Int. Cl.³ .................. F16K 21/18; F16K 31/18
[52] U.S. Cl. .......................... 137/391; 128/214 C;
    128/214.2; 137/433; 251/122
[58] Field of Search .............. 137/391, 430, 433;
    251/121, 122; 128/214 C, 214 R, 214.2, 227

[56]    References Cited
    U.S. PATENT DOCUMENTS

| 843,069 | 2/1907 | Burdick | 137/433 |
|---|---|---|---|
| 2,090,273 | 8/1937 | Wagner | 137/391 |
| 2,315,109 | 3/1943 | Cutter | 128/214 C |
| 2,599,286 | 6/1952 | Rockwell | 251/122 |
| 2,602,464 | 7/1952 | Greening | 137/391 |
| 2,696,818 | 12/1954 | Van Loghem | 128/214 C |
| 3,033,323 | 5/1962 | La Manna | 251/121 |
| 3,776,229 | 12/1973 | McPhee | 128/214 C |
| 3,963,024 | 6/1976 | Goldowsky | 128/214 C |
| 3,989,043 | 11/1976 | Dimeff | 137/430 |
| 4,096,879 | 6/1978 | Seruretal | 137/433 |

FOREIGN PATENT DOCUMENTS

| 2282278 | 8/1974 | France | 128/214 C |
| 817387 | 7/1959 | United Kingdom | 128/214 C |

Primary Examiner—Martin P. Schwadron
Assistant Examiner—G. L. Walton
Attorney, Agent, or Firm—Hubbell, Cohen, Stiefel & Gross

[57]    ABSTRACT

A device for regulating the flow of liquid through a liquid line communicating with a reservoir disposed thereabove comprises a housing defining a float chamber having inlet and outlet openings in the top and bottom walls thereof, respectively; a substantially egg-shaped float disposed in the chamber for vertical movement between an upper position and a lower position; upper valve means connected to the float for closing the inlet opening when the float is in its upper position and lower valve means connected to the float for closing the outlet opening when the float is in its lower position, the valve means being in close spaced relation with the top and bottom walls of the chamber throughout the range of movement of the float; and means disposed beneath the chamber for regulating the flow of liquid through the outlet opening.

13 Claims, 6 Drawing Figures

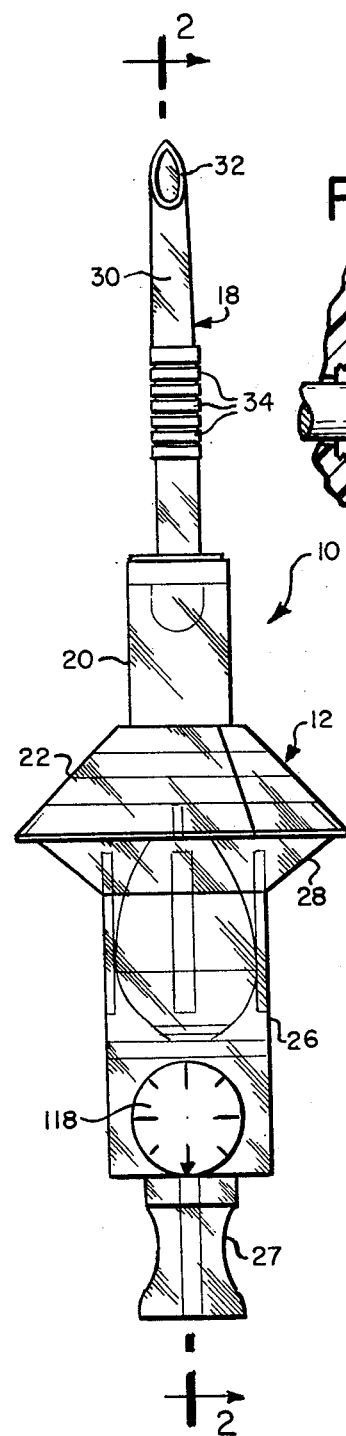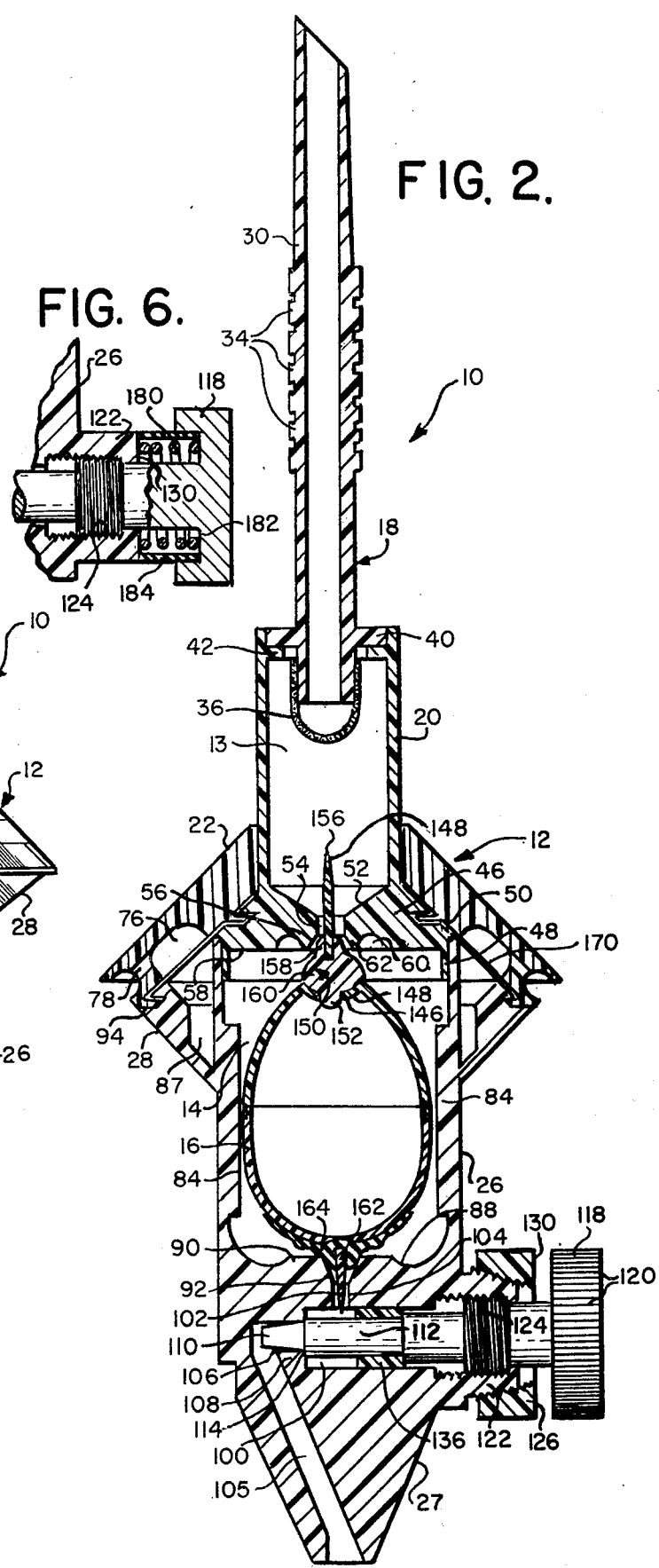

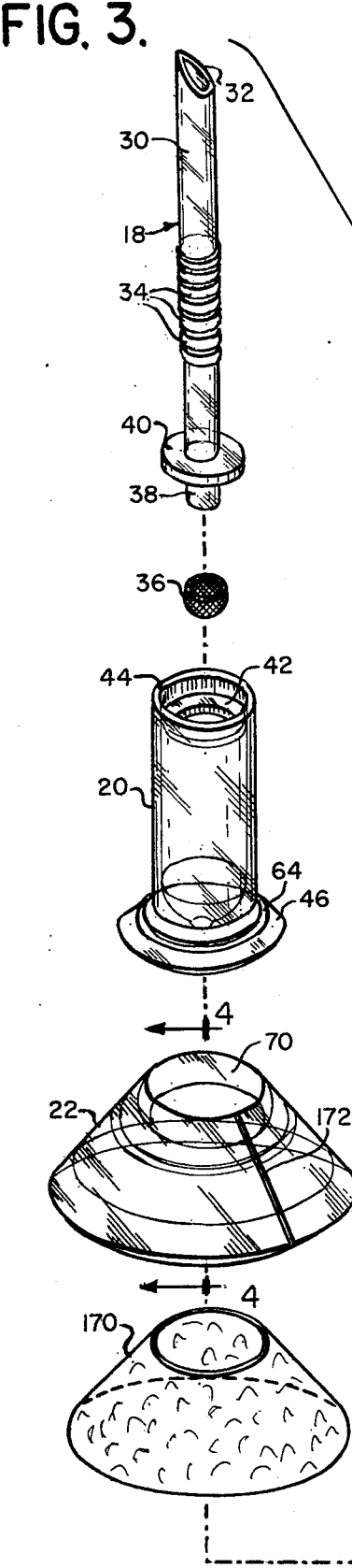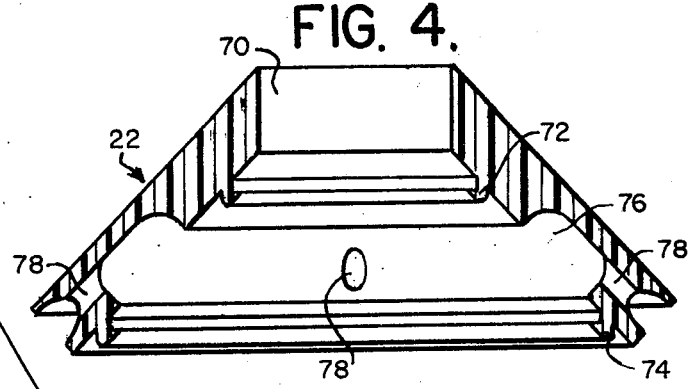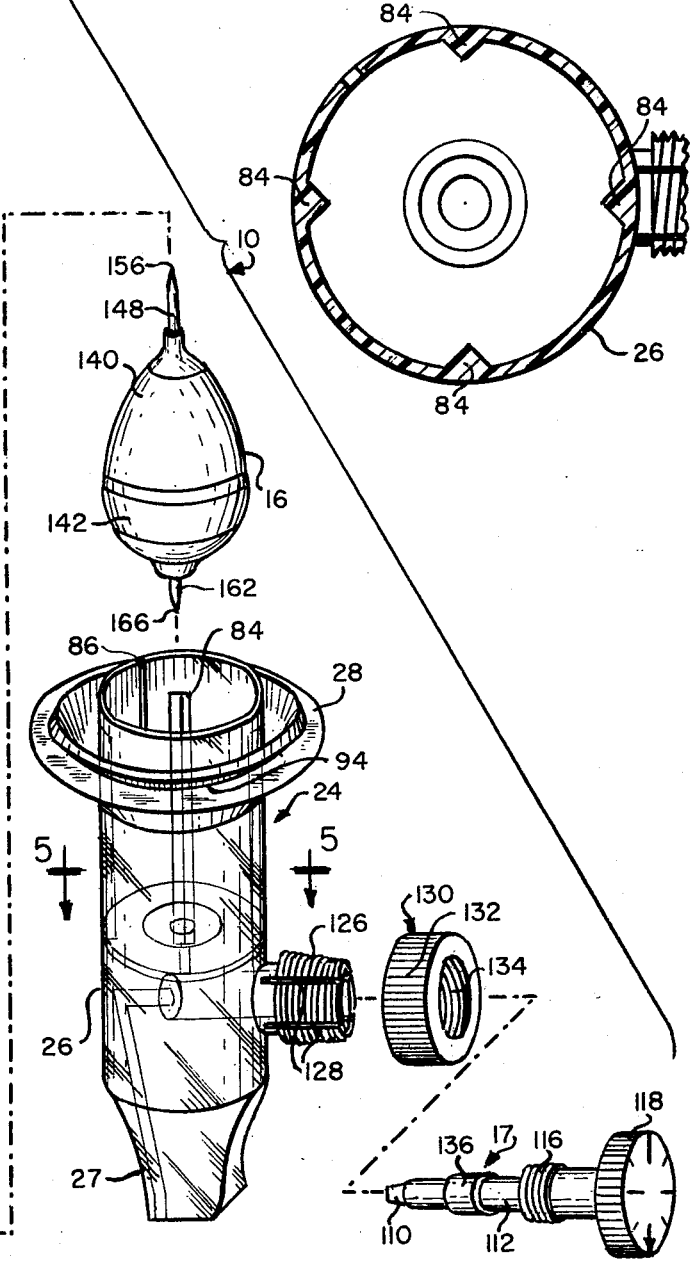

CONSTANT FLOW DEVICE

BACKGROUND OF THE INVENTION

1. Field of the Invention

This invention pertains generally to apparatus for regulating the flow rate from a liquid reservoir into a patient's vascular system and more particularly to such apparatus of the type including a float chamber for isolating the flow rate from the head pressure in the reservoir.

2. Statement of the Prior Art

Devices for regulating the rate of liquid flow from a reservoir into a patient's vascular system are well known. Most commonly, such devices are used to regulate liquid flowing under the influence of gravity from a reservoir through a flexible conduit terminating in a needle or cannula disposed in the patient's vein. In their simplest form, such devices comprise an adjustable clamp or the like secured on the flexible conduit. By counting the number of drops passing through the conduit over a given period of time, the infusion rate may be determined and the clamp adjusted to the desired rate. Typically, a drip chamber is interposed in the conduit to facilitate observation of the flow rate.

One of the principal drawbacks of such basic devices is that they do not isolate the flow rate from the changing head pressure in the reservoir. Thus, where accurate dosing is required, such devices must be constantly monitored and adjusted.

In an improved class of infusion devices, a float arrangement is disposed between the reservoir and the clamp. Typically, such float arrangements include a float chamber having inlet and outlet ports which communicate, respectively, with the reservoir and the flexible conduit leading to the patient. A float disposed in the chamber is connected to valves which open and close the inlet and outlet ports in response to changes in the level of liquid in the chamber. The flow rate to the patient is thus isolated from the head pressure in the reservoir. Examples of such devices may be found in U.S. Pat. Nos. 2,090,273, 3,989,043 and in commonly assigned U.S. patent application Ser. No. 596,974 filed July 18, 1975, now abandoned, and commonly assigned copending U.S. application Ser. No. 883,261, filed Mar. 3, 1978. Other infusion devices incorporating float arrangements may be found in U.S. Pat. Nos. 2,784,733, 2,538,662, 2,844,147, 3,042,038, 3,105,511, 3,311,268, 3,667,464, 3,738,361, 3,756,233, 3,931,818 and 3,963,024.

Although such devices effectively isolate the flow rate from the reservoir, it will be apparent that the flow rate will, to some extent, be dependent on the head pressure in the float chamber. In applications requiring highly accurate dosing, changes in the flow rate resulting from variations in the head pressure in the float chamber may be unacceptable. The prior art solutions to this problem are inadequate, mostly because they are unduly complex.

As noted above, it is common to employ a pinch-type clamp along the length of flexible tubing connecting the float chamber to the needle inserted in the patient's vascular system. However, because of the memory of the flexible tubing and the resulting delays in changing the flow rate when the clamp is adjusted, it has been suggested to employ a needle valve and housing therefor in place of the clamp. See, for example, British Pat. No. 817,387 issued to Fletcher et al and U.S. Pat. No. 3,605,740 issued to Price et al. One of the problems with these arrangements is that they fail to compensate for suction forces which act on the valve as a result of liquid flow through the tube leading to the patient. Even a slight change in the spacing between the needle valve and its seat will vary the flow rate and hence reduce the accuracy of the device.

It is well known that when the float arrangement is used, the chamber must be vented to the outside to permit the escape of air upon entry of liquid into the chamber and vice versa. The desirability of disposing a filter in the air vent to prevent the entry of contaminants and the escape of liquid has been suggested. See, for example, U.S. Pat. No. 3,756,233 issued to Goldowsky and U.S. Pat. No. 3,989,043 issued to Dimeff. One of the drawbacks of the prior art arrangements is that the vent communicates with the filter through a relatively small surface area of the latter thus increasing the air resistance through the vent. This, in turn, can effect both the entry and exit of liquid in the float chamber and hence the liquid flow rate to the patient.

Various valve arrangements have been suggested for closing the outlet passage from the float chamber when the chamber is completely empty. It will be apparent that this valve must provide an air tight seal to prevent the entry of air into the patient's vascular system. While arrangements employing elastomeric valves or valve seats have been suggested to effect better seating (see, for example, U.S. Pat. No. 3,963,024 issued to Goldowsky, U.S. Pat. No. 3,105,511 issued to Murphey, and commonly assigned U.S. application Ser. No. 883,261 filed Mar. 3, 1978), prior art arrangements do not provide effective sealing when the float and attached valve are tilted relative to the valve seat. Such arrangements are somewhat improved when ribbing or the like is provided on the internal walls of the chamber for maintaining proper alignment of the float and attached valve relative to the valve seat. See, for example, U.S. Pat. No. 3,931,818 issued to Goldowsky and commonly assigned co-pending application Ser. No. 883,261 filed Mar. 3, 1978. However, because of the requirement that the float be free-sliding within the chamber, the ribs do not completely avoid valve alignment problems.

SUMMARY OF THE INVENTION

According to the present invention, I have developed a precision liquid flow regulation device particularly adapted for incorporation in intraveneous infusion apparatus.

The device according to the invention includes a float arrangement for isolating the flow rate to the patient from the head pressure in the reservoir and a needle valve assembly for regulating the flow rate from the float chamber to the patient. The chamber is provided with inlet and outlet ports for accommodating liquid flow in and out of the chamber, respectively, and valves are connected to the float at its upper and lower ends for opening and closing the ports as the vertical position of the float in the chamber varies in response to changes in the liquid level therein. According to one aspect of the invention, the valves are in close confronting relation with their respective valve seats throughout the range of movement of the float. As a result, the change in the liquid level in the chamber required to move the float between its uppermost and lowermost positions is quite small thereby maintaining the liquid level in the chamber at a substantially constant level.

In order to insure that the float will assume substantially the same position in the chamber for any given liquid level therein, the various components of the device are configured to minimize factors which would otherwise affect the float position. For example, according to the invention, the float is substantially egg-shaped to avoid both the accumulation of liquid on the upper surface of the float and the accumulation of air bubbles on the undersurface of the float. For the same reason, the surfaces of the valves are curved rather than flat. The occurrence of capillary forces between the float and the internal walls of the float chamber, which forces could also have an undesirable effect on the float position, are avoided by providing sufficient space between these members.

The preferred needle valve assembly comprises a needle valve connected to one end of a stem having external threads which mate with corresponding internal threads in the valve housing. A knob is secured to the other end of the stem which protrudes through an opening in the housing, whereby rotation of the knob effects axial movement of the needle valve. According to the invention, the effect of suction forces on the axial position of the needle valve is minimized by providing means for fixing the axial position of the needle valve once its desired position has been set. The preferred means comprises an internally threaded nut which mates with external threads on a projection of the housing in surrounding relation with the free end of the stem. Once the desired position of the needle valve is set, the nut is rotated until it abuts the knob, thereby locking the knob, and hence the connected stem and needle valve, against inward axial movement. It will be appreciated, however, that other arrangements, some of which will be suggested hereinafter, may also be used for this purpose.

According to another aspect of the invention, the housing for the device includes a diamond shaped portion near the top of the float chamber defined by upper and lower frustoconical members. The upper and lower frustoconical members are provided with confronting internal recesses which communicate both with the float chamber and outside air via air passages provided for this purpose. A filter disposed between the confronting faces of the upper and lower frustoconical members extends between the recesses. Because the use of the frustoconical members allows the confronting recesses to be made fairly wide, the area of the filter exposed to passing air is quite large. Thus, the resistance to air flow in and out of the float chamber is minimized, the result being an even, unhindered flow of liquid in and out of the float chamber.

Other features and advantages of the constant flow device according to the present invention will be more fully apparent from the following detailed description and annexed drawings of the preferred embodiment thereof.

BRIEF DESCRIPTION OF THE DRAWINGS

In the drawings:

FIG. 1 is a front elevation of the preferred constant flow device according to the present invention;

FIG. 2 is a sectional view taken substantially along the lines 2—2 in FIG. 1;

FIG. 3 is an exploded perspective view of the preferred constant flow device of FIGS. 1 and 2;

FIG. 4 is a sectional view of the preferred cover member taken substantially along the lines 4—4 in FIG. 3;

FIG. 5 is a sectional view taken substantially along the lines 5—5 in FIG. 3;

FIG. 6 is a fragmentary sectional view illustrating an alternative arrangement for securing the axial position of the needle valve.

DETAILED DESCRIPTION OF THE PREFERRED EMBODIMENT

Referring now to the drawings, and initially to FIGS. 1-3 thereof, the preferred constant flow device in accordance with the present invention is generally designated at 10. The device 10 is particularly intended for incorporation in an intravenous infusion arrangement of the type wherein liquid disposed in a reservoir flows under the influence of gravity through a flexible tube or the like connected at one end to the reservoir and at the other end to a needle or cannula inserted in the patient's vascular system. It will be apparent, however, that the device 10 may be utilized in other applications where highly accurate liquid flow rate regulation is desired. As shown, the principal components of the preferred device 10 are a housing 12 defining a vision chamber 13 and a float chamber 14, a substantially egg-shaped float 16 disposed in chamber 14, and valve assembly 17 for regulating the rate of liquid flow out of chamber 14.

While it will be appreciated hereinafter that the housing 12 may assume a variety of configurations, the housing 12 illustrated in FIGS. 1-3 is preferred. As best shown in FIG. 3, housing 12 includes a connecting member 18, an upper cylindrical member 20, a frustoconical cover 22 and a lower portion 24 comprised of an inverted frustoconical member 28 and a lower cylindrical member 26 having a tapered bottom portion 27.

As presently preferred and shown, the connecting member 18 comprises a tube 30 adapted to be secured at one end 32 to a liquid reservoir (not shown) disposed thereabove. For this reason, the end 32 is preferably beveled to accommodate insertion in a rubber stopper or the like. The external wall of the tube 30 is preferably provided with a plurality of annular splines 34 to facilitate handling. To remove foreign matter carried by liquid flowing from the reservoir, a coarse filter 36 is preferably secured, as by a suitable adhesive, over the opening at the lower end 38 of the tube 30. Filter 36 may comprise a metal screen. The tube 30 also preferably includes an annular shoulder 40 adjacent its lower end which mates with a corresponding internal annular shoulder 42 adjacent the upper end 44 of the upper cylindrical member 20 when the device 10 is assembled (FIG. 2). Preferably, the connecting member 18 is fixedly secured to the member 20 by joining the shoulders 40 and 42 with a suitable adhesive.

As shown, the member 20 defines the vision chamber 13. The lower end of the preferred member 20 is formed with a frustoconical flange 46 terminating in a depending cylindrical wall 48. As best shown in FIG. 2, wall 48 is preferably stepped back from the widest portion of the flange 46 for defining a shoulder 50. The bottom wall 52 of the member 20 is preferably funnel-shaped for collecting liquid in the central portion of the bottom of the chamber 13. Liquid flows out of chamber 13 through an opening 54 in the bottom wall 52 which communicates with the chamber 13 at the focal point of the funnel. For reasons that will be apparent hereinafter, the lower portion 56 of the opening 54 is preferably widened and the undersurface 58 of the bottom wall 52 is preferably provided with an annular recess 60 for defining a boss 62 adjacent the portion 56. Also for reasons that will be apparent hereinafter, the outer surface of the flange 46 is preferably provided with an annular groove 64.

Referring to FIGS. 2-4, the frustoconical cover 22 has an opening 70 which, as best shown in FIG. 3, is dimensioned to fit about the cylindrical portion of the member 20. A pair of spaced annular ribs 72 and 74 project inwardly from the internal wall of the cover 22, the rib 72 mating with the annular recess 64 in the lower portion of the member 20 when the device 10 is assembled (FIG. 2). For reasons that will be explained below, the inner surface of the cover 22 is provided with a preferably continuous annular recess 76 which communicates via one or more spaced ducts, shown by way of example as four equally spaced ducts 78, with the bottom edge of the cover 22 (FIG. 4).

Referring now to FIGS. 2, 3 and 5, the lower cylindrical member 26 of the housing portion 24 defines the generally cylindrical float chamber 14. As presently preferred and shown, a plurality of spaced longitudinally extending ribs shown by way of example as four equally spaced ribs 84, project inwardly from the internal wall of the member 26 into the chamber 14. As will be apparent hereinafter, the ribs 84 serve as guides for the float 16 during movement thereof in chamber 14. The upper portion of the member 26 is provided with a vent, shown by way of example as a single longitudinal slot 86 which communicates with the space 87 between the member 26 and the frustoconical member 28. As best shown in FIG. 2, the bottom defining wall 88 of the preferred cylindrical member 26 has a centered annular boss 90 defining a hemispherical opening 92 in the center thereof. The inverted frustoconical member 28 is preferably integrally formed with the member 26 and, as best shown in FIG. 2, is preferably provided with a continuous circumferentially extending groove 94 adjacent its upper edge, the groove 94 mating with the projection 74 in the cover 22 when the device 10 is assembled.

Referring again to FIGS. 2 and 3, the housing for the preferred valve assembly 17 is preferably formed in the tapered portion 27 of the housing 12. However, this is not necessary and valve assembly 17 and the housing therefor could be formed separately and connected to opening 92 below chamber 14 by a flexible tube or the like. As shown, valve assembly 17 is disposed in a passage 100 which communicates with the opening 92 via a narrowed cylindrical opening 102 defined by the annular shoulder 104. The passage 100, which is preferably perpendicular to the axis of the member 26, communicates at its inner end with a downwardly extending passage 105 which, in use, will communicate at its lower end with a flexible tube or the like leading to the patient's vascular system. As shown, the passage 100 has a narrow portion 106 defined by a shoulder 108 which serves as a seat for the valve. The preferred valve is a needle valve comprising a tapered cylindrical member 110 connected to an axially aligned stem 112. The stem 112 is preferably greater in diameter than the valve 110 and thus defines an annular shoulder 114 at its point of connection with the valve. The shoulder 114 is wider than the internal diameter of shoulder 108 and thus serves to limit movement of the needle valve 110 into the passage portion 106. The stem 112 is externally threaded at 116 adjacent its outer end and a knob 118 for rotating the stem 112 is connected to the free end thereof. The knob preferably has axial splines 120 or the like for facilitating rotation thereof.

As shown, the outer end of the passage 100 is defined by an annular projection 122. The outer wall of the projection 122 is tapered and the projection has both internal and external threads at 124 and 126, respectively. For reasons that will be apparent hereinafter, the projection 122 is preferably provided with one or more axially extending slots, shown by way of example as four equally spaced slots 128. For reasons to be explained below, device 10 preferably includes a nut 130 having an externally splined wall 132 and a tapered internally threaded wall 134, the threads 134 mating with the external threads 126 on the projection 122 when device 10 is assembled (FIG. 2). A seal 136 is preferably disposed about the stem 112 for restricting both the entry of bacteria into the passage 100 and the escape of liquid out of the passage. The seal 136 may comprise, for example, the seal disclosed in my application Ser. No. 957,076, filed Nov. 2, 1978.

As best shown in FIG. 2, the preferred egg-shaped float 16 is hollow and comprises upper and lower halves 140 and 142, respectively, joined together at their confronting edges by, for example, a suitable adhesive. Preferably, the top of the upper part 140 is provided with a recess 144 having an opening 146 in the center thereof and an upper valve rod 148 having a rounded base 150 is secured in the recess 144 as by a suitable adhesive. As shown, the base 150 preferably has a downwardly depending projection 152 which mates with the opening 146 for securely fixing the position of the valve rod 148 relative to the float. The valve rod 148 is preferably tapered to a point at its free end 156 and the base 150 preferably has an upper portion 158 and a lower, widened portion 160. Consequently, the ball like, or conical upper end of float 16 matches the corresponding structure defining opening 54. Valve rod 148 and base 150 may be formed integrally. Alternatively, and as presently preferred, the valve rod 148 and base may be formed separately, the rod being secured in an aperture in the base as by a suitable adhesive. A lower valve rod 162 also having a rounded base 164 is preferably secured to the lower end of the float 16. Like the rod 148, the rod 162 is preferably tapered towards its free end 166 although it need not be tapered to a point as the rod 148 preferably is. Again, the rod 162 and base 164 are preferably formed separately and then joined together by securing the rod in an aperture in its base, the base being joined to the float 16 by, for example, a suitable adhesive. When the device 10 is assembled, the rods 148 and 162 are in axial alignment with the longitudinal axis of the float 16 (FIG. 2).

While various materials may be used, housing 12, valve assembly 17 and nut 130 are all preferably comprised of a suitable rigid plastic. Most preferably, the plastic will be a clear plastic so that liquid flow through the device 10 can be observed. In any event, at least the member 20 which defines the vision chamber 13 should be comprised of a clear plastic. To avoid breakage during use, float 16 and the narrow portions of the valve rods 148 and 162 are preferably comprised of a slightly elastomeric material such as a slightly elastomeric plastic. For reasons that will be explained below, the base portions 150 and 164 of the valve rods 148 and 162, respectively, are preferably formed of an elastomeric material such as, for example, rubber, latex, or a silicone rubber. Seal 136 is also preferably comprised of an elastomeric material.

Referring now to FIGS. 2 and 3, the device 10 may be assembled by first disposing the float 16 and attached rods 148 and 162 in the chamber 14 such that the lower rod 162 extends through the openings 92 and 102 in the bottom 88 of the member 26. Cylindrical member 20, connecting member 18 and coarse filter 36 may then be connected and disposed on top of the member 26 with the upper edge of the member 26 abutting the shoulder 50 on the member 20. A filter 170, having the same general configuration as the cover 22, may then be disposed inside the cover. As will be apparent hereinafter, air flowing in and out of chamber 14 must pass through filter 170. Filter 170 should also preclude contaminants from entering the chamber 14 and liquid from leaving the chamber. A suitable material for filter 170 is silicon impregnated filter paper. With filter 170 in place in cover 22, the cover may be slid over connecting member 18 and cylindrical member 20 into confronting relation with the lower frustoconical member 28. The cover 22 is then forced downward until the projections 72 and 74 snap into the annular groove 64 in the cylindrical member 26 and the annular groove 94 in the frustoconical member 28, respectively. As best shown in FIG. 3, the cover 22 may be provided with a slot 172 in the manner of a snap ring to prevent breakage of the cover during assembly and disassembly of the device 10.

With the cover 22 in place, it will be apparent that the filter 170 is trapped between the cover 22 and the confronting faces of the cylindrical member 26 and frustoconical member 28. It will also be apparent that the filter 170 is held firmly at its edges by the projections 72 and 74. At this point, the nut 130 may be threaded onto the projection 122 at which time slots 128 permit flexing of projection 122 thereby avoiding damage thereto. Assembly of the device 10 is completed by threading valve assembly 17 into the passage 100. At this point, the device 10 is ready for use. It is included in the infusion system by connecting the member 18 to the liquid reservoir and the passage 104 to a flexible tube or the like leading to the patient's vascular system. The knob 118 is then rotated to select the desired flow rate through passage portion 106. As presently preferred and best shown in FIGS. 1 and 3, the knob 118 is provided with markings indicating the number of drops per minute flowing through the passage portion 106 for any given position of the valve 110. For example, one full turn of the knob 118 may vary the drop rate through the passage portion 106 from zero to one hundred drops per minute. Accordingly, the threads 116 and 126 should be smoothed and polished. Once the knob 118 is rotated to the desired position, the nut 130 is rotated until it abuts the knob 118 thereby preventing further movement of the valve 110 into the passage portion 106. The reason for this will be more fully explained below. The rate of liquid flow through the passage portion 106 may be checked by observing the number of drops flowing through vision chamber 13.

In the absence of liquid in the chamber 14, the base 164 of the rod 162 will seat on the boss 90. To prevent air from passing from the chamber 14 into the patient's vascular system, it is important that the seal formed by the base 164 seating on the boss 90 be hermetic. Accordingly, and as already noted, the base 164 should be formed of an elastomeric material. Alternatively, the boss 90 could be comprised of an elastomeric material.

To further insure a hermetic seal, and as already noted, the base 164 is rounded as is the opening 92. For example, both may assume a substantially hemispherical shape. It will thus be apparent that even if the float 16 is slightly displaced from a truely vertical position, the opening 92 nevertheless will be hermetically isolated from the passage 100.

Liquid from the reservoir will flow first through the tube 30 and then into coarse filter 36. If desired, the size of the opening at the bottom 38 of the connecting member 18 may be reduced as compared with the lumen thereof whereby the size of the drop exiting connecting member 18 may be controlled. In any event, as liquid passes through the filter 36 and enters the vision chamber 13, it will collect in the funnel-shaped bottom of the member 20 and begin to pass through opening 54 into float chamber 14. As liquid flows into the chamber 14, air escapes by following the route through the slot 86, space 87, filter 170 and slots 78. It will be apparent that a large area of the filter 170 is exposed to passing air, i.e. the filter portion overlying the annular recess 76. This insures a low air resistance and hence an even flow of liquid into chamber 14.

The float 16 and the connected base members 150 and 164 are dimensioned such that when the base member 164 is seated on the boss 90, the flow passage through opening 54 into chamber 14 is open. The buoyancy of the float 16 is selected such that when a sufficient quantity of liquid is collected in the chamber 14, the float 16 will begin to rise. It is presently preferred that the float 16 will begin to rise when the chamber 14 is approximately three-quarters full. As the float 16 rises, the base 164 separates from the boss 90 thus opening the liquid passage through the opening 92 into the passage 100. During movement, the float is maintained in a substantially vertical position both by the ribs 84, which are in close spaced relation with the widest portion of the float 16, and the valve rods 148 and 162. It will thus be apparent that either the valve rods or the ribs may be eliminated. The preferred device, however, includes both.

Assuming that the rate of liquid flow into the chamber 14 exceeds the flow rate out through opening 92, the float 16 will rise until the widened portion 160 of the base 150 seats in the widened portion 56 of opening 54. As already noted, and as is the case with base 164 and opening 92, base 150 and opening 56 are both preferably rounded to facilitate better seating. However, unlike the seal formed by seating base 164 in opening 92, the seal formed by seating base 150 in opening 56 need not be hermetic. The seal should be sufficient, however, to prevent the entry of liquid into chamber 14. As liquid continues to flow out through the opening 92, the float 16 will begin to move downward thus permitting additional liquid to flow from chamber 13 into float chamber 14. When the reservoir empties, the liquid level in the chamber 14 will gradually decrease until float 16 is once again returned to its lowermost position in which opening 54 is closed by base portion 164. As already noted, this preferably occurs when the chamber 14 is about three-quarters full.

As is apparent from FIG. 2, the dinamic range of movement of the float 16 in the chamber 14 is quite small, typically about 1 mm. Accordingly, the change in liquid volume and level in the chamber 14 required to move the float 16 between its uppermost and lowermost functional positions is also quite small. Thus, the static head pressure in the float chamber 14 will remain relatively constant and thus will have little effect on the liquid flow rate through the opening 102 and into the patient's vascular system. Because of the limited range of movement of float 16, it is important to insure that the float 16 will assume substantially the same position for any given volume of liquid in the chamber 14. Otherwise, the level of fluid in chamber 14 will not remain constant thus reducing the accuracy of the device 10. Therefore, it is important that other factors that may affect the position of the float 16 be eliminated to the maximum extent possible. Two undesirable factors which may affect the position of float 16 are the accumulation of liquid on the top of the float and the accumulation of air bubbles under the float. According to the present invention, the effect of these factors is reduced by selecting a substantially egg-shaped float and rounded base portions 150 and 164 for connecting the rods 148 and 162 to the float 16. In the preferred embodiment of the present invention, the angle formed by the uppermost portion of the egg-shaped float with its longitudinal axis is preferably about 45°. It will thus be apparent that liquid flow off the top of the float 16 will be substantially unhindered as will the upward movement of any air bubbles which may accumulate in the liquid surrounding the lower half of the float. The rod 148 is preferably tapered at its free end 156 to prevent the accumulation of liquid droplets on top of the rod which could also effect the weight and hence position of the float 16 in the chamber 14. The base portion 150, rods 148 and 162 and float 16 may all be fabricated from a suitable plastic. Preferably, the surfaces of the float 16, valve rods 148 and 162, and base portions 150 and 164 are polished to remove nicks, crevices, etc. in which liquid or air bubbles could accumulate. If desired, these surfaces may also be treated with a suitable liquid deterrent.

Another undesirable factor which could effect the position of the float 16 in chamber 14 is the occurrence of capillary forces between the external wall of the float 16 and the internal wall of the member 26. Accordingly, the spacing between the float 16 and the defining wall of the chamber 14 is preferably sufficiently large to avoid such forces. For example, the spacing may be 1-2 mm. Capillary forces may also be created between the rod 148 and the defining wall of the opening 54, which forces would tend to hold the float in its upper position. This may be avoided by providing sufficient spacing between the rod 148 and the wall defining opening 54. However, it is also apparent that liquid flowing through the opening 54 will exert some force on the float 16 as it strikes the base portion 150. Accordingly, the opening 54 should be sufficiently small to minimize this downward force but sufficiently large to avoid capillary force. For example, if the widest diameter of rod 148 is 1 mm, the diameter of opening 54 may be 1.8 mm.

Still another undesirable factor which could effect the position of the float 16 in the chamber 14 is the occurrence of capillary forces between the defining walls of the opening 102 and the lower valve rod 162 which forces would tend to hold the float 16 in its lower position. Accordingly, the spacing between the rod 162 and the wall defining the opening 102 should be sufficient to avoid the occurrence of such forces. However, it will also be apparent that the downward flow of liquid through the passage 105 will create suction force which will tend to draw the float downwards. Since the effect of this suction force on the float 16 is dependent on the surface area of the float exposed to the force, it is desirable to keep the opening 102 as small as possible.

Accordingly, the size of the opening 102 must be sufficiently small to minimize the suction force but sufficiently large to avoid capillary forces. If, for example, the widest diameter of rod 162 is 1.8 mm, the diameter of the opening 102 may be 2.2 mm.

It will be appreciated that apart from the liquid level in the chamber 14, the accuracy of the liquid flow rate to the patient's vascular system is also dependent on the accuracy with which the needle valve 110 regulates the size of the opening through the passage portion 106. It is therefore desirable to preclude, to the maximum extent possible, unwanted changes in the axial position of the needle valve 110. As already noted, during liquid flow through the passage 105, a suction force is created. This suction force will act on the needle valve 110 to draw the valve further into the passage portion 106. Since those skilled in the art will appreciate that there is always some tolerance between mating threads, such as the threads 126 and 134, variations in the suction force acting on the needle valve 110 could result in variations in the size of the opening through the passage portion 106. According to the present invention, movement of the needle valve 110 under the influence of such suction forces is avoided by the nut 130, which, as is above described, is tightened against the knob 118 once the desired flow rate has been set. Referring now to FIG. 6, as an alternative to the nut 130, a coil spring 180 may be used. One end of the coil spring 180 may be secured to the free end of the projection 122 and the other end seated in a groove 182 in the confronting face of the knob 118. To further restrict the entry of contaminants into the passage 100, the spring may be enclosed by a suitable flexible material such as rubber 184. It will be apparent that the spring force should be greater than the maximum anticipated suction force acting on needle valve 110 but not so large that damage to the stem 112 or knob 118 may result.

While I have herein shown and described the preferred embodiment of a constant flow device according to the present invention and have suggested certain modifications thereto, it will be appreciated that other changes and modifications may be made without departing from the spirit and scope of the invention. Accordingly, the above description should be construed as illustrative and not in a limiting sense, the scope of the invention being defined by the following claims:

I claim:

1. In a device for regulating the flow of liquid through a liquid line communicating with a reservoir disposed thereabove, said device being of the type comprising: walls defining a closed chamber having a top wall, a bottom wall spaced below said top wall, and a side wall extending between said top and bottom walls, said top wall defining an opening for introducing liquid from said reservoir to said chamber and said bottom wall defining an opening for discharging liquid therefrom; a float disposed in said chamber for vertical movement therein between an upper position and a lower position; said walls having an air vent in the upper portion thereof in spaced relation with said float in its range of movement between said upper and lower positions; upper valve means connected to said float for closing said top opening when said float is in said upper position and lower valve means connected to said float for closing said bottom opening when said float is in said lower position; and means disposed beneath said bottom for regulating the flow of liquid through said bottom opening; wherein the improvement comprises:

said float being substantially egg-shaped and disposed in said chamber with its thickened end in confronting relation with said bottom wall to minimize the accumulation of air bubbles on the lower portion of said float and its narrowed end in confronting relation with said top wall to minimize the accumulation of liquid on the upper portion of said float; and said upper valve means being configured to minimize the accumulation of liquid thereon and said lower valve means being configured to minimize the accumulation of air bubble thereon.

2. The device according to claim 1, and further comprising first and second rods connected at one end to the upper and lower ends of said float, respectively, said first and second rods being aligned with the longitudinal axis of said float and extending, respectively, into said top and bottom openings in said chamber for the full range of movement of said float between said upper and lower positions.

3. The device according to claim 2, wherein said rods are tapered, the free ends of said rods being narrower than their connected ends.

4. The device according to claim 1, and further comprising a vertically extending rib secured to the internal surface of said side wall for guiding said float in its range of movement between said upper and lower positions.

5. The device according to claim 1, wherein the inner surface of said bottom wall has a hemispherical recess concentric with said bottom opening;

said lower valve means comprises a substantially hemispherical projection secured to the lower end of said float with its rounded surface facing downwards; and either the portion of said bottom defining said hemispherical recess or said projection is comprised of an elastomeric material.

6. The device according to claim 1, wherein said means for regulating the rate of liquid flow through said bottom opening comprises: a housing defining a thru-passage communicating with said bottom opening, said passage having a narrow portion;

a needle valve; and means for moving said valve in and out of said narrow portion for varying the size of the liquid path therethrough.

7. The device according to claim 6, wherein said needle valve moving means comprises:

said housing having an opening communicating with said passage;

a stem threadably secured to said housing in said opening, said stem being connected at one end to said needle valve, the other end of said stem protruding through said opening;

a knob secured to the free end of said stem for effecting axial movement of said needle valve; and further comprising means for securing said needle valve in a predetermined position.

8. The device according to claim 7, wherein said needle valve securing means comprises:

the surface of said knob confronting said housing having an annular recess therein; and a coil spring disposed about said stem, said spring having one end seated on said housing and the other end seated in said recess.

9. The device according to claim 8, further comprising a flexible member secured to said spring in surrounding relation therewith along the entire length thereof.

10. The device according to claim 7, wherein said needle valve securing means comprises:

said housing including an externally threaded annular projection in surrounding relation with said other end of said stem; and an internally threaded annular member threadably secured on said projection, said annular member being movable into abutting relation with said knob for securing said needle valve in said predetermined position.

11. The device according to claim 1, and further comprising:

a frustoconical member disposed about the upper portion of said chamber, said member having a recess in the inner wall thereof in communication with said vent, and a thru-opening communicating with said recess; and a filter overlying all of said recess.

12. The device according to claim 11, wherein said recess extends continuously along said inner surface.

13. The device according to claim 12, and further comprising another frustoconical member secured about said chamber beneath said first mentioned frustoconical member and in confronting relation therewith; and means for detachably securing said frustoconical members together.

* * * * *